(12) United States Patent
Teepe

(10) Patent No.: US 12,121,733 B2
(45) Date of Patent: Oct. 22, 2024

(54) ENERGY GENERATION FROM TINY SOURCES

(71) Applicant: CELTRO GMBH, Dresden (DE)

(72) Inventor: Gerd Teepe, Dresden (DE)

(73) Assignee: Celtro GmbH, Dresden (DE)

(*) Notice: Subject to any disclaimer, the term of this patent is extended or adjusted under 35 U.S.C. 154(b) by 359 days.

(21) Appl. No.: 17/774,032

(22) PCT Filed: Nov. 3, 2020

(86) PCT No.: PCT/EP2020/080791
§ 371 (c)(1),
(2) Date: May 3, 2022

(87) PCT Pub. No.: WO2021/089530
PCT Pub. Date: May 14, 2021

(65) Prior Publication Data
US 2023/0006468 A1  Jan. 5, 2023

(30) Foreign Application Priority Data

Nov. 4, 2019 (EP) .................................... 19206852

(51) Int. Cl.
*A61N 1/375* (2006.01)
*A61M 37/00* (2006.01)
(Continued)

(52) U.S. Cl.
CPC ..... *A61N 1/37512* (2017.08); *A61M 37/0015* (2013.01); *A61N 1/362* (2013.01);
(Continued)

(58) Field of Classification Search
None
See application file for complete search history.

(56) References Cited

U.S. PATENT DOCUMENTS

| 2011/0300821 A1* | 12/2011 | Wang ....................... H04B 1/18 |
| | | 455/232.1 |
| 2017/0179732 A1* | 6/2017 | Hoeppner ........... H02J 7/00045 |
| 2019/0072532 A1* | 3/2019 | Willett ............... G01N 33/0062 |

FOREIGN PATENT DOCUMENTS

| EP | 2426311 A2 | 3/2012 |
| JP | 08098510 | 4/1996 |
| WO | 2017208231 A1 | 12/2017 |

* cited by examiner

*Primary Examiner* — Jared Fureman
*Assistant Examiner* — Joel Barnett
(74) *Attorney, Agent, or Firm* — Olson & Cepuritis, Ltd.

(57) ABSTRACT

The invention discloses a device for collection of tiny charges in the Nano-Coulomb-range and below, comprising at least one capacitor stack build by n capacitors and 2n switches (n∈N), at least one further capacitor outside the capacitor stack as buffer capacity, at least two additional switches and a DC input source. The n capacitors are dedicated to be sequentially charged by the DC input source one after the other, wherein the 2n switches in the capacitor stack couple the n capacitors sequentially to the DC input source. The at least one further capacitor is dedicated to be charged from the n capacitors of the capacitor stack at once. Furthermore, the invention discloses a method for small charge collection, comprising the steps of sequentially charging the n capacitors of the at least one capacitor stack by coupling one capacitor after the other to the DC input source by selectively closing the switches and discharging the n capacitors of the capacitor stack into at least one further capacitor outside the capacitor stack (n∈N). Additionally, the usage of the device or the method according to the invention to collect charges from sources with electrical potentials of a few millivolts is disclosed.

16 Claims, 16 Drawing Sheets

(51) Int. Cl.
*A61N 1/362* (2006.01)
*A61N 1/372* (2006.01)
*A61N 1/378* (2006.01)
*H02J 7/00* (2006.01)
*H02J 7/34* (2006.01)
*H02J 50/00* (2016.01)
*H02J 50/10* (2016.01)

(52) U.S. Cl.
CPC ....... *A61N 1/37235* (2013.01); *A61N 1/3785* (2013.01); *H02J 7/0013* (2013.01); *H02J 7/345* (2013.01); *H02J 50/001* (2020.01); *H02J 50/10* (2016.02); *H02J 2207/50* (2020.01); *H02J 2310/23* (2020.01)

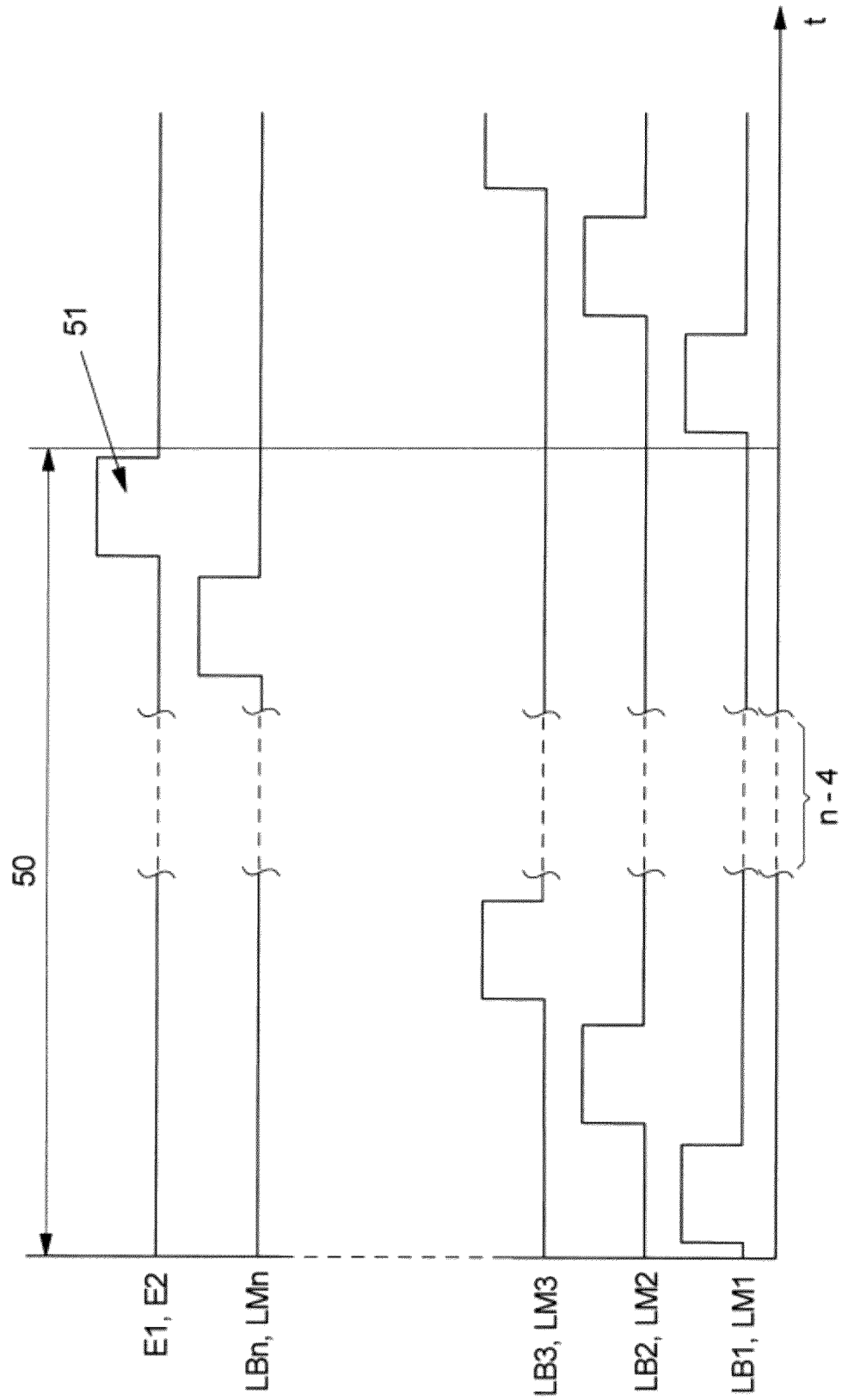

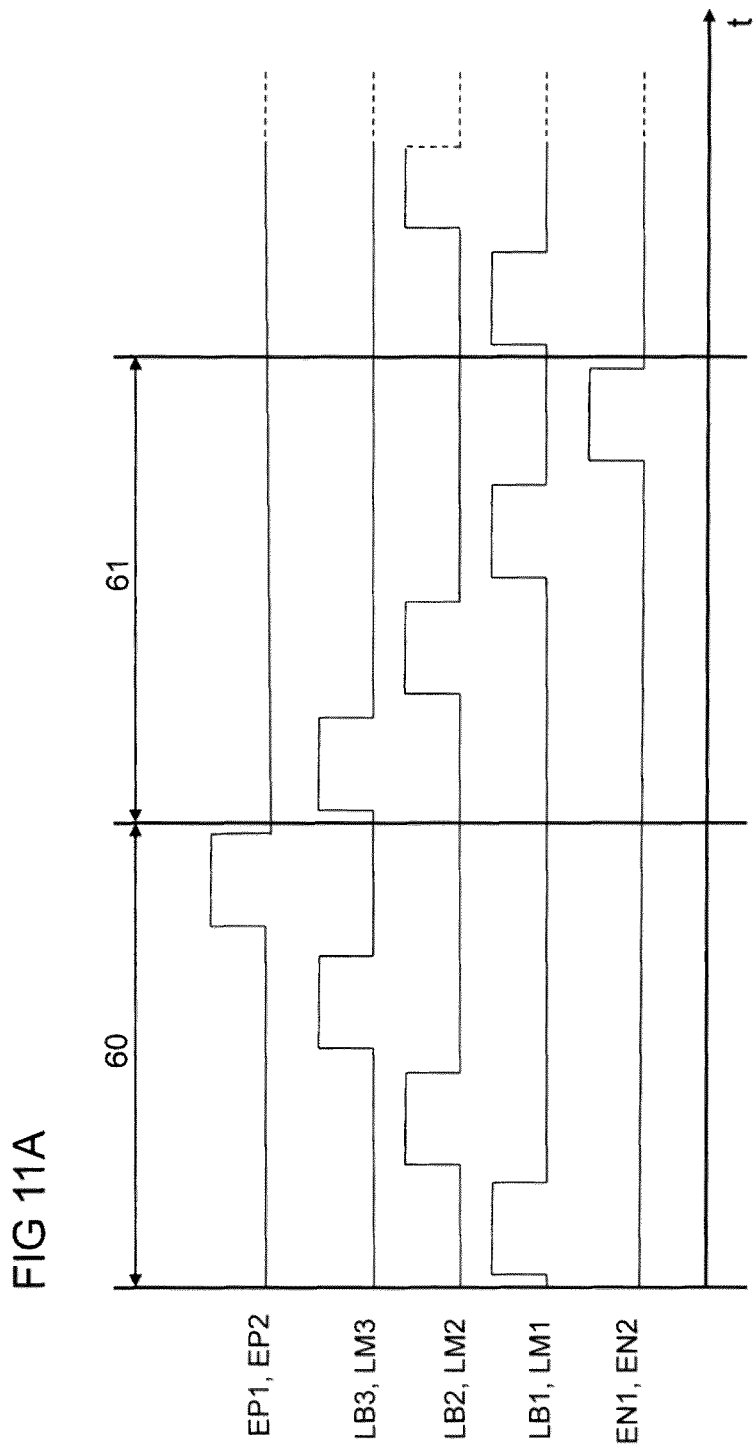

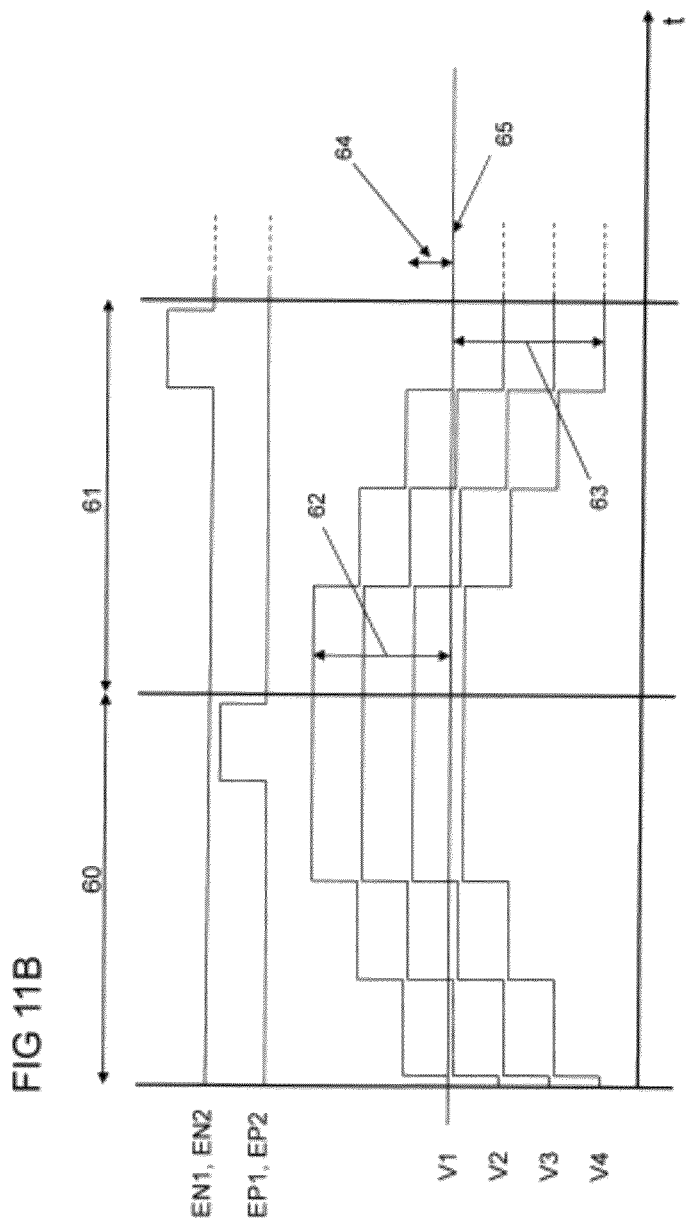

ENERGY GENERATION FROM TINY SOURCES

CROSS-REFERENCE TO RELATED APPLICATIONS

This application is a U.S. National Stage of PCT/EP2020/080791, filed Nov. 3, 2020, claiming priority to EP Application No. 19206852.6 filed Nov. 4, 2019, both of which are incorporated herein by reference.

The invention discloses a device for collection of tiny charges in the Nano-Coulomb-range and below, comprising at least one capacitor stack build by n capacitors and 2n switches (n∈N), at least one further capacitor outside the capacitor stack as buffer capacity, at least two additional switches and a DC input source. The n capacitors are dedicated to be sequentially charged by the DC input source one after the other, wherein the 2n switches in the capacitor stack couple the n capacitors sequentially to the DC input source. The at least one further capacitor is dedicated to be charged from the n capacitors of the capacitor stack at once. Furthermore, the invention discloses a method for small charge collection, comprising the steps of sequentially charging the n capacitors of the at least one capacitor stack by coupling one capacitor after the other to the DC input source by selectively closing the switches and discharging the n capacitors of the capacitor stack into at least one further capacitor outside the capacitor stack (n∈N). Additionally, the usage of the device or the method according to the invention to collect charges from sources with electrical potentials of a few millivolts is disclosed.

Due to the rapid miniaturization of portable electronics, such as cell phones, hand held computing devices, wireless sensors, remote monitoring applications, medical devices and so on, the availability of reliable power sources remains an important technical issue. Batteries are frequently used as power sources but they always bring along the need of recharging or replacement. In more and more applications recharging or replacement of batteries is economically and logistically impractical, laborious, or potentially dangerous.

For example, batteries are used as power supply in pacemakers. If the life time of the battery is over, it must either be recharged or even be replaced by a new one. Conventional recharging systems use for example magnetic induction (U.S. Pat. No. 3,867,950 A1) or solar cells (US 2009326597 AA). These systems suffer from the fact that additional technical devices outside the patient's body must be used to charge the pacemaker, which still makes it necessary to check the pacemaker's performance status and perform a battery charging procedure either by a technician or by the patient if necessary. A procedure which is usually unfavorable for the patient.

Another aspect is the so called Internet of Things (IoT) which is of growing interest. IoT describes a system of interrelated computing devices, mechanical and digital machines, objects, animals or people that are provided with unique identifiers enabling the transfer of data over a network without requiring human-to-human or human-to-computer interaction. Naturally those unique identifiers need wireless power supply and it is highly desirable if no recharging by an external power source (e.g. power outlet) or even replacement of the power supply is necessary.

Therefore, it would be of high economic interest to provide a power supply for such applications which need not to be recharged by an external power source like a power outlet or be replaced. This would make such applications independent of external power sources. Furthermore, in cases where battery recharging or replacement is inconvenient or even potentially dangerous for a user, as in the case of pacemakers, a major step towards greater security could be taken.

Therefore, it is the purpose of the invention to overcome the above mentioned disadvantages of the state of the art and to provide a device which can be used as a power source and which must not be recharged by an external power source or be replaced.

Therefore, the invention provides a device and a method to collect small charges from electrical energy sources e.g. from the surrounding environment in the amount that a power supply can be provided for portable electronics, wherein the small voltage levels of the source themselves are too low to be used as power supply for any kind of portable electronics. The invention targets electrical energy sources like bioelectric signals, radio signals, thermal sources or vibrations, which means the electrical energy voltage levels are in the range of a few millivolt.

The present invention provides a device for charge collection comprising
  at least one capacitor stack built by n capacitors and 2n switches;
  at least one further capacitor outside the at least one capacitor stack as buffer capacitor;
  at least two additional switches outside the at least one capacitor stack;
  a DC input source;
  a CMOS-Logic;
  wherein the 2n switches of the at least one capacitor stack couple the n capacitors selectively to the DC input source;
  wherein the n capacitors of the at least one capacitor stack are dedicated to be sequentially charged by the DC input source one after the other;
  wherein the at least one further capacitor outside the at least one capacitor stack is dedicated to be charged from the n capacitors of the capacitor stack at once; and
  wherein n∈N.

Furthermore, the present invention provides a method for charge collection, comprising at least one capacitor stack build by n capacitors and 2n switches, at least one further capacitor outside the capacitor stack as buffer capacitor, at least two additional switches and a DC input source, comprising the steps
  the n capacitors of the capacitor stack are sequentially charged by coupling one capacitor after the other to the DC input source by selectively closing the switches;
  discharging the n capacitors of the capacitor stack into the at least one further capacitor outside the capacitor stack;
  wherein n∈N.

Additionally, the usage of the device according the invention or the method according to the invention to collect charges from sources with electrical potentials of a few millivolts is disclosed.

DETAILED DESCRIPTION

The device according to the invention comprises at least one DC input source. The DC input source has an electric potential of a few millivolts. Preferably the electric potential of the DC input source is between 1 mV and 100 mV, more preferably between 1 mV and 50 mV, most preferably between 1 mV and 10 mV.

Suitable energy sources with electrical potentials in this range are for example bioelectric signals, radio signals, thermal sources or vibrations. In one embodiment of the invention bioelectric signals from nerve potential are used as DC input. Bioelectric signals of nerve cells have typically an electric potential of 60 mV and an internal resistance of 20 to 200 kOhm.

In a preferred embodiment of the invention the device is dedicated to collect small charges in the Nano-Coulomb-range and below.

Furthermore, the device according to the invention comprises at least one capacitor stack, wherein the capacitor stack is built by n capacitors and 2n switches, wherein n∈N. The capacitor stack can comprise as much capacitors as can be accommodated constructively. In one embodiment of the invention n is between 2 and 20, more preferably between 2 and 14. The n capacitors of the capacitors stack are dedicated to be sequentially charged by the DC input source one after the other.

The 2n switches of the capacitor stack couple the n capacitors selectively to the DC input source in a way that every capacitor is sequentially charged by the DC input source one after the other. The controlling and sequencing of the switches is generated from a usual CMOS-Logic, which is common to Microelectronics.

At least one further capacitor is situated outside the capacitor stack, which works as a buffer capacitor. According to the invention, the at least one further capacitor is dedicated to be charged from the n capacitors of the at least one capacitor stack at once. In a preferred embodiment of the invention, the device comprises one further capacitor outside the capacitor stack as buffer capacitor. In a further preferred embodiment of the invention the device comprises two further capacitors outside the capacitor stack as buffer capacitors.

Furthermore, the device comprises at least two additional switches outside the capacitor stack. In a preferred embodiment of the invention the device comprises two additional switches outside the capacitor stack. The additional switches are dedicated to selectively couple the capacitor stack to the at least one further capacitor outside the capacitor stack or to a further capacitor stack.

In a further preferred embodiment the device comprises four additional switches outside the capacitor stack. Preferably the device comprises four additional switches outside the at least one capacitor stack if the device comprises a first further capacitor outside the at least one capacitor stack and a second further capacitor outside the at least one capacitor stack. In this embodiment two additional switches are dedicated to selectively connect the at least one capacitor stack to the first further capacitor outside the capacitor stack and the two further additional switches are dedicated to selectively connect the at least one capacitor stack to the second further capacitor outside the capacitor stack.

Accordingly, in one preferred embodiment the device according to the invention comprises two further capacitors outside the capacitor stack as buffer capacitors outside the at least one capacitor stack and four additional switch outside the at least one capacitor stack.

From its physical construction as a stack, then capacitors of the capacitor stack are all connected in series electrically. Furthermore, in one embodiment of the invention, the at least one capacitor stack comprises at least three conductive plates wherein the conductive plates have a top-side and a bottom-side and wherein the top-side of at least one conductive plate is part of a first capacitor and the bottom-side of the at least one conductive plate is part of a neighboring further capacitor. Furthermore, the capacitor stack comprises an isolating material between the conductive plates in a way that a capacitor is built.

In a preferred embodiment of the invention, a capacitor stack with n capacitors comprises m=n+1 conductive plates. According to the invention the first conductor n=1 is built between the bottom-side of the first conductive plate (m=1) and the top-side of the second conductive plate (m=2). The neighboring conductor (n=2) is built between the bottom-side of the second conductive plate (m=2) and the top-side of the third conductive plate (m=3) and so on.

The capacitance of the capacitors built according to the invention is quite wide ranging from 1 nF down to 1 fF and even below. It depends on plate geometries and the dielectric material employed between the plates.

The arrangement of the conductors in a capacitor stack with n capacitors according to the invention has the advantage that the inner conductive plates, which means plates m=2 to m=n form no or just very small parasitic capacitances to the outside of the stack. Parasitic capacitances are well known in the art. They arise at the interfaces of capacitors to the surrounding and are unwanted as those have to be charged at every charge cycle of the capacitor. This process lowers the charging efficiency of the capacitor and therefore its end-charging voltage. Accordingly, in the state of the art every capacitor has two interfaces to the surrounding and therefore two interfaces where parasitic capacitances arise.

The capacitor stack according to the invention is able to provide n capacitors, wherein only the first and the last capacitor have a substantial interface to the surrounding. Therefore, advantageously, only at these two interfaces parasitic capacitances will form. Accordingly, the charging efficiency of the n capacitors of the capacitor stack is increased as well as the end-charging voltage.

Furthermore, in a preferred embodiment of the invention, all capacitors are connected in series electrically.

In one preferred embodiment of the invention the device is an integrated circuit wherein switches are realized as transistors and capacitors are realized by conductive plates from integrated circuit technology.

Preferably the conductive plates are made of material selected from the group comprising metal or polysilicon or any other conductive material from integrated circuit technology. Suitable metals are copper and aluminum and tungsten.

In one embodiment of the invention the isolating material is selected from the group comprising $SiO_2$, $SiN$ and $Hf_2O$ and stacks thereof.

As described above the capacitor stack is internally nearly perfect if it comes to storing the applied charges, as the field is nicely confined internally. Unfortunately at the first and last conductive plates still some parasitic capacitances will form. In view not to lose the energy stored in those external parasitic capacitances, according to the invention, an inductor can be applied to perform intermediate storage in a resonant circuit configuration.

Accordingly, in one embodiment of the invention the device comprises additionally an inductor.

Preferably small inductors are integrated monolithically in the integrated circuit. According to the invention the switching frequency is chosen high enough so that the resonant frequency of the parasitic capacitor and the inductivity equals the inverse of the total charging/discharging cycle time of the capacitor stack. In addition the charging/discharging timing of the capacitor stack should be adapted such that a sine-curve is approximated.

Practical inductivity values in integrated circuits will be in the range 1-10 µH when 100 windings will wrap around a typical chip of 25 mm² size. Parasitic capacitor values will range between 1-10 pF for a typical capacitor stack. For this setting, the resonance frequencies will be found between 10-200 MHz. The charging frequencies of the capacitances in the capacitor stack in consequence will have to be 2n higher.

In another preferred embodiment the device comprises several capacitor stacks wherein every capacitor stack is dedicated to charge another capacitor stack and one capacitor stack is dedicated to charge at least one further capacitor outsides the capacitor stacks. Thereby, cascading of the sequential small charge collection according to the invention is possible.

Several capacitor stacks are preferably connected by switches outside the capacitor stacks, most preferably always two capacitor stacks are connected by two switches outside the capacitor stacks. In one embodiment of the invention the device comprises x capacitor stacks and 2x switches outside the capacitor stacks. In one embodiment of the invention the device comprises 1 to 20 capacitor stacks, preferably 5 to 15, most preferably 13 to 15, as this is within the capabilities of current semiconductor production technologies.

However, the charging frequency of a further capacitor stack is n-times slower than the charging frequency of the first capacitor stack (with n being the number of capacitors in the first capacitor stack). In principle the n capacitors of the first capacitor stack are charged by the DC input source one after the other. Afterwards the n capacitors of the first capacitor stack are discharged at once to one capacitor of a further capacitor stack. In case the further capacitor stack is built by k capacitors, k charging cycles are needed to charge the k capacitors of the further capacitor stack one after the other. If all capacitors of the further capacitor stack are charged they are discharged to a further capacitor outside the capacitor stack at once. In total, the entire discharge occurs at a frequency k·n lower than the charging frequency of the first capacitor stack. The maximum voltage of the second stack is k·n the feeding voltage of the DC input source. For example with 10 mV at the DC input source, and 10 capacitors on each capacitors stack, 1 V can be realized as output at maximum.

According to the invention, every further capacitor stack is dedicated to be fed by positive or negative voltages from another capacitor stack. Therefore, the switches outside the capacitor stacks connecting the capacitor stacks have to be sequenced accordingly. If the first capacitor stack provides positive or negative charge, charging of the second capacitor stack has to be done accordingly.

If bioelectric signals from nerve potential are used as source for small charges, the device according to the invention provides a needle or a needle bed in contact with nerve cells as DC input source. Thereby, the device according to the invention enables the collection of low charges from multiple cells in the tissue. According to the invention, the needles of the needle bed are isolated against each other and connected through to the back-side by soldering bumps. An integrated circuit ideally has a solder bump at the same location, so that a connection can be made from a needle to an input on an integrated circuit. The input functions as DC input source according to the invention.

Accordingly, in a preferred embodiment of the invention, the DC input source is a needle or a needle bed in contact with nerve cells, wherein the needles of the needle bed are isolated against each other and connected through to the back-side by a soldering bump. As described above, the needle or the needles of the needle bed are connected to a capacitor stack by a soldering bump.

As semiconductor circuit technology is easily scalable, the device according to the invention can easily be multiplied up to the number of needles of the needle bed. Preferably the needle bed has 2-2000 needles, more preferably 50-1500 and most preferably 100-1000 needles. In a preferred embodiment of the invention, an integrated circuit is provided with the same number of devices, according to the invention, as the number of needles of the needle bed.

Therefore, in another preferred embodiment of the invention, the DC input source is a needle bed in contact with nerve cells, wherein every needle of the needle bed is connected to a capacitor stack by a soldering bump.

In an embodiment of the invention the sequencing of the switches is generated from a usual CMOS-Logic, which is common to Microelectronics. For the CMOS-logic to function, voltages of a few hundred millivolts are required. Typical state of the art semiconductor technology operates at around 1 Volt or slightly below. Since the device according to the invention collects energy starting with a few millivolts at the source, this voltage is too low to operate the CMOS-logic.

However, after collection and cascading, voltages in the 1-Volt domain can be obtained, which is enough to operate the CMOS-logic. For this reason, a startup circuit is required, to make sure the logic can be powered and the switches are operated to perform energy collection from the tiny sources.

For this, a magnetic coupling over coils is proposed. The outer coil is excited with alternate current, creating a magnetic alternating field. Through this field the startup energy is transmitted to the coil on the integrated circuit, which recuperates the startup energy.

In a preferred embodiment of the invention, the device additionally comprises a coil, which is dedicated to receive a startup energy by magnetic coupling with another coil.

A further aspect of the invention concerns a method for collecting charges, especially for collecting small charges in the Nano-Coulomb range and below. The advantages and advantageous embodiments according to the invention also apply to the method according to the invention and vice versa.

Furthermore, the invention provides a method for charge collection, comprising at least one capacitor stack build by n capacitors and 2n switches, at least one further capacitor outside the capacitor stack as buffer capacitor, at least two additional switches and a DC input source, comprising the steps the n capacitors of the capacitor stack are sequentially charged by coupling one capacitor after the other to the DC input source by selectively closing the switches;
discharging the n capacitors of the capacitor stack into the at least one further capacitor outside the capacitor stack;
wherein n∈N.

In a preferred embodiment of the invention small charges in the Nano-Coulomb-range and below are collected.

In a preferred embodiment of the method of the invention the n capacitors of the capacitor stack are sequentially charged one after the other in n charging cycles and the n capacitors of the capacitor stack are discharged in an n+1$^{st}$ cycle into at least one further capacitor outside the capacitor stack at once.

Fundamentally, the capacitors of a capacitor stack could be charged in any order. However, in order to reduce the recharging of the parasitic capacitances which arise at the interfaces to the surrounding, the following charging scheme is proposed. According to a preferred embodiment of the invention, the n capacitors of the capacitor stack are sequentially charged one after the other in n charging cycles, wherein the first capacitor is charged, afterwards the capacitor which is next to the first one is charged, afterwards the capacitor which is next to the one charged before is charged until all n capacitors are charged.

If all capacitors of a capacitor stack are charged, the capacitors of the capacitor stack are all discharged into at least one further capacitor outside the capacitor stack at once. This is done by selectively closing the switches of the capacitor stack and the switches outside the capacitor stack.

In a further embodiment of the invention a bipolar charging of the capacitor stack can be done. Fundamentally, each capacitor of a capacitor stack can be charged to positive or negative voltages, depending which plate of the capacitor is grounded. As already described, capacitors in the capacitor stack are being loaded sequentially. While one plate is grounded, the other plate is charged to a fraction of the input voltage. Which means, that capacitors in the capacitor stack above the currently grounded plate are pushed to positive voltages, whereas the plates below the currently grounded plate are pushed to negative voltages. Accordingly, the capacitors of the capacitor stack can be charged to positive or negative voltages, by closing the switches inside the capacitor stack in an appropriate manner, thereby selecting the grounded plate of the each capacitor in the capacitor stack.

If bipolar charging of the capacitor stack is done, preferably two further capacitors outside the capacitors stack are used as buffer capacitors. In this embodiment of the invention the at least one capacitor stack is first charged with positive voltages and after all capacitors in the capacitor stack are charged, all capacitors of the capacitor stack are discharged into the first further capacitor outside the capacitor stack. Afterwards the capacitors of the capacitor stack are charged with negative voltages and after all capacitors in the capacitor stack are charged all capacitors of the capacitor stack are discharged into the second further capacitor outside the capacitor stack.

Since parasitic capacitances which arise at the interfaces to the surrounding have also to be charged at each charging procedure, it is most advantageous to always charge neighboring capacitor and not to "jump around" between the capacitors in the capacitor stack. Therefore, if bipolar charging of the capacitor stack is done the capacitors of the capacitor stack are sequentially charged the n capacitors are discharged into a first further capacitor outside the capacitor stack, afterwards the n capacitors of the capacitor stack are sequentially charged in the reversed order and after the n capacitors are charged the n capacitors are discharged into a second further capacitor outside the capacitor stack.

Accordingly, in a preferred embodiment of the invention after the n capacitors of the capacitor stack are sequentially charged the n capacitors are discharged into a first further capacitor outside the capacitor stack, afterwards the n capacitors of the capacitor stack are sequentially charged in the reversed order and after the n capacitors are charged the n capacitors are discharged into a second further capacitor outside the capacitor stack.

According to the invention the n capacitors of a capacitor stack can be discharged at once into one capacitor of a further capacitor stack.

The charging sequence for the second capacitor stack is derived from the first stack and couples to its timing. Instead of discharging the first capacitor stack into a buffer capacitance, it is discharged into one of the capacitors forming the second capacitor stack. Fundamentally it could be any of capacitors of the second capacitor stack, but practically the charging of the second capacitor stack should follow the same method already described. Which means charging of the capacitors of a capacitor stack should be done by charging neighboring capacitors. As the second capacitor stack is also loaded with some parasitic capacitance to the outside, sequentially charging the second stack as described will keep the charge flown into the parasitic capacitances to a minimum at each step.

One of the embodiments of the discharge circuit is a bipolar setting. This allows the charging of the second capacitor stack with negative and positive charge depending on the sequence.

When the negative charge is transferred to the second capacitor stack, care has to be taken that the transistor switches are operated such that the charge on the stack is added with reverse polarity, so that this charge is accumulated on the second stack and not subtracted.

Parallelizing the sequential charge collection according to the invention, energy collection is multiplied and therefore the output-power of the device is increased.

The invention is further described by 13 figures and three examples.

Figure 3A:
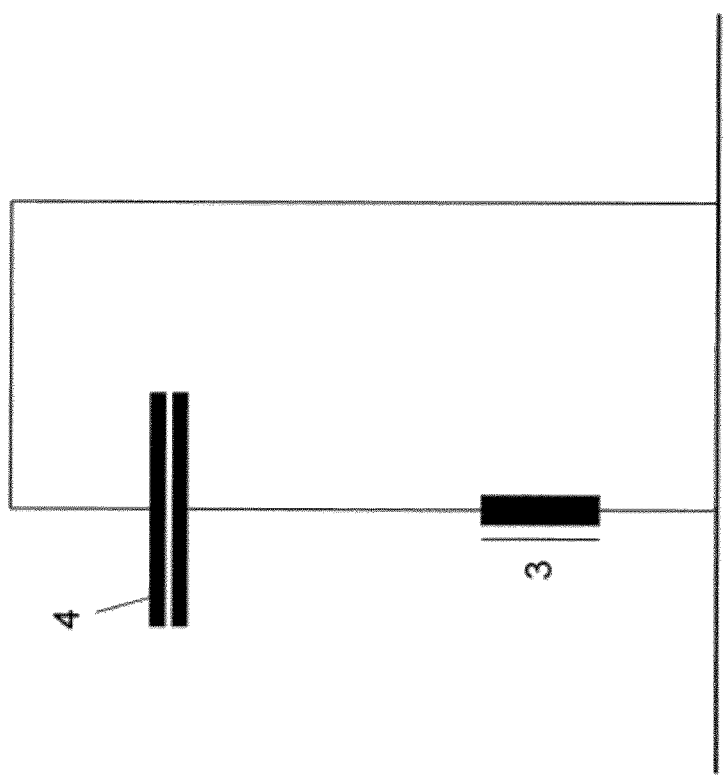
Figure 4:
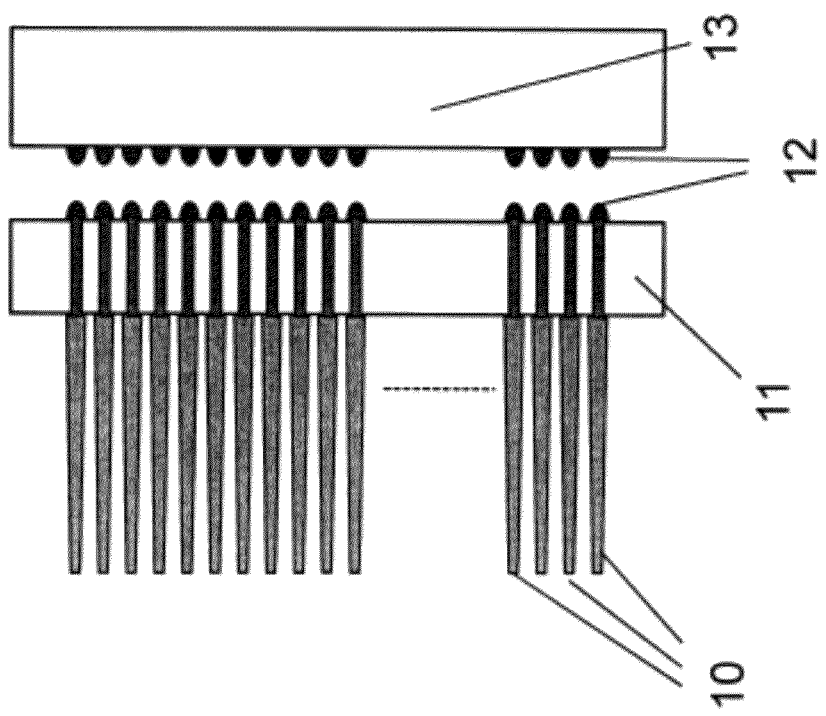
Figure 5:
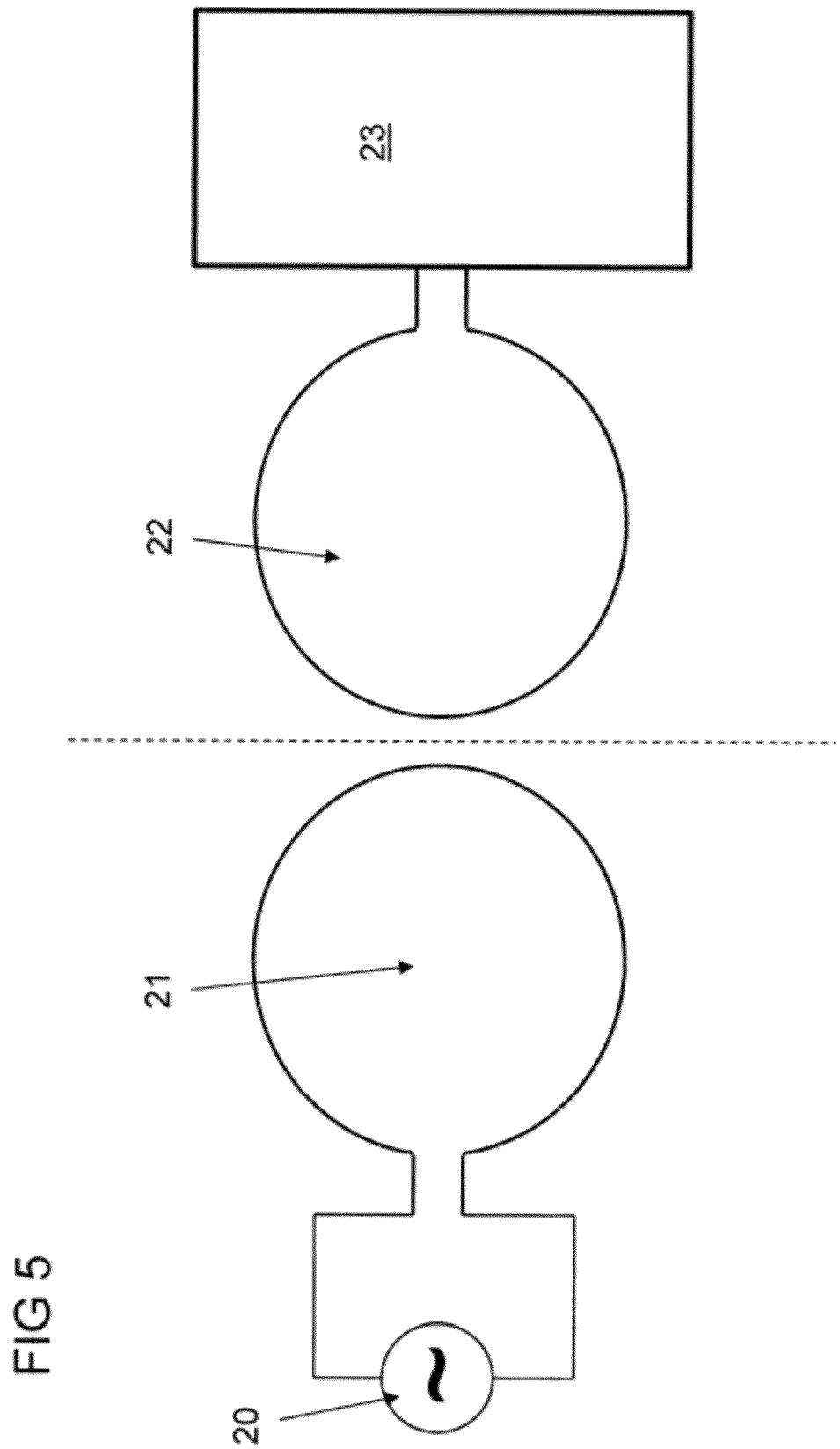
Figure 6:
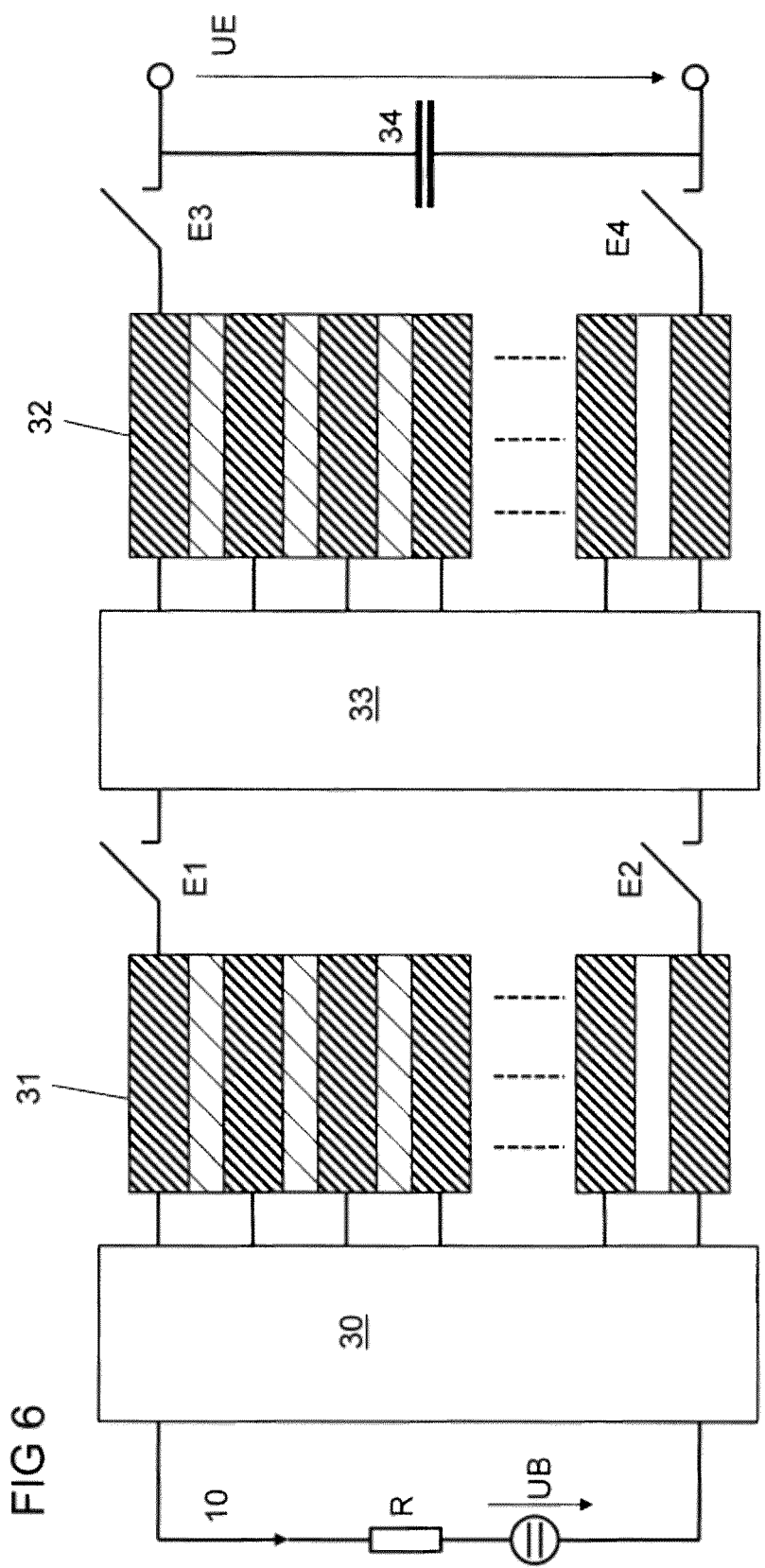
Figure 7:
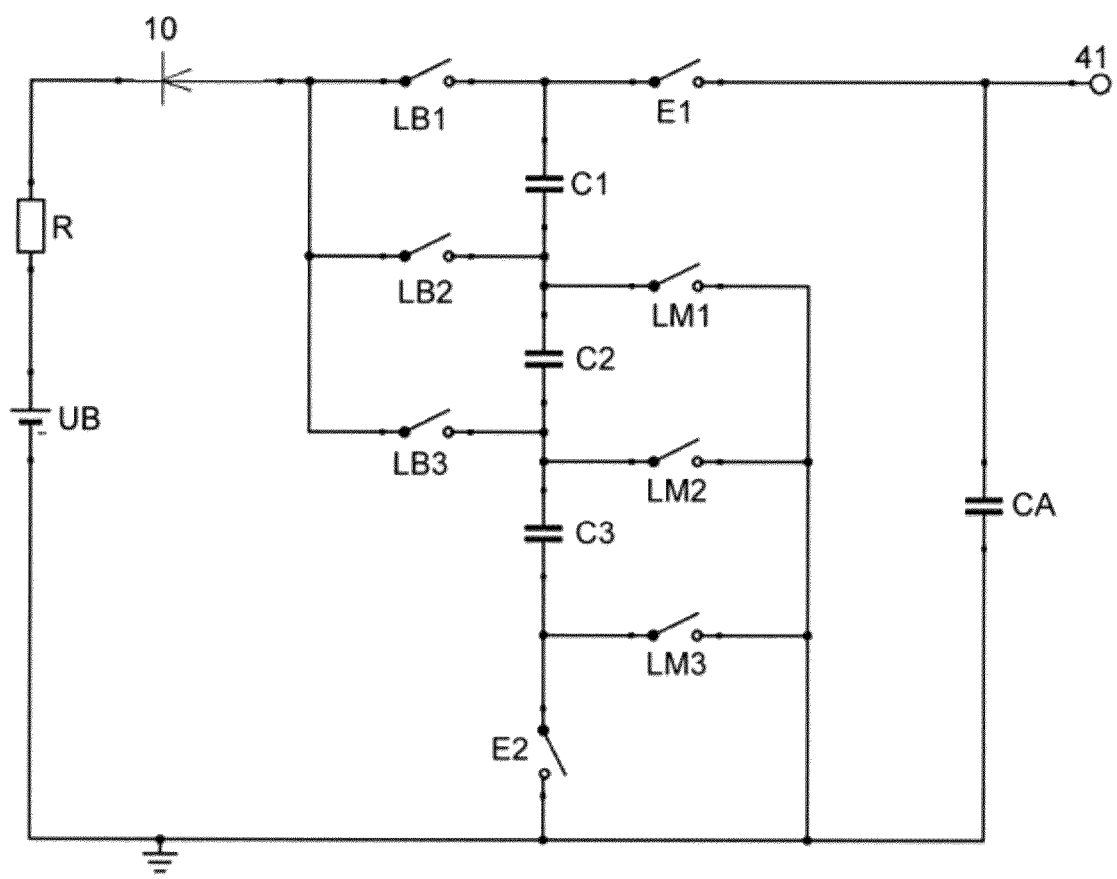
Figure 8A:
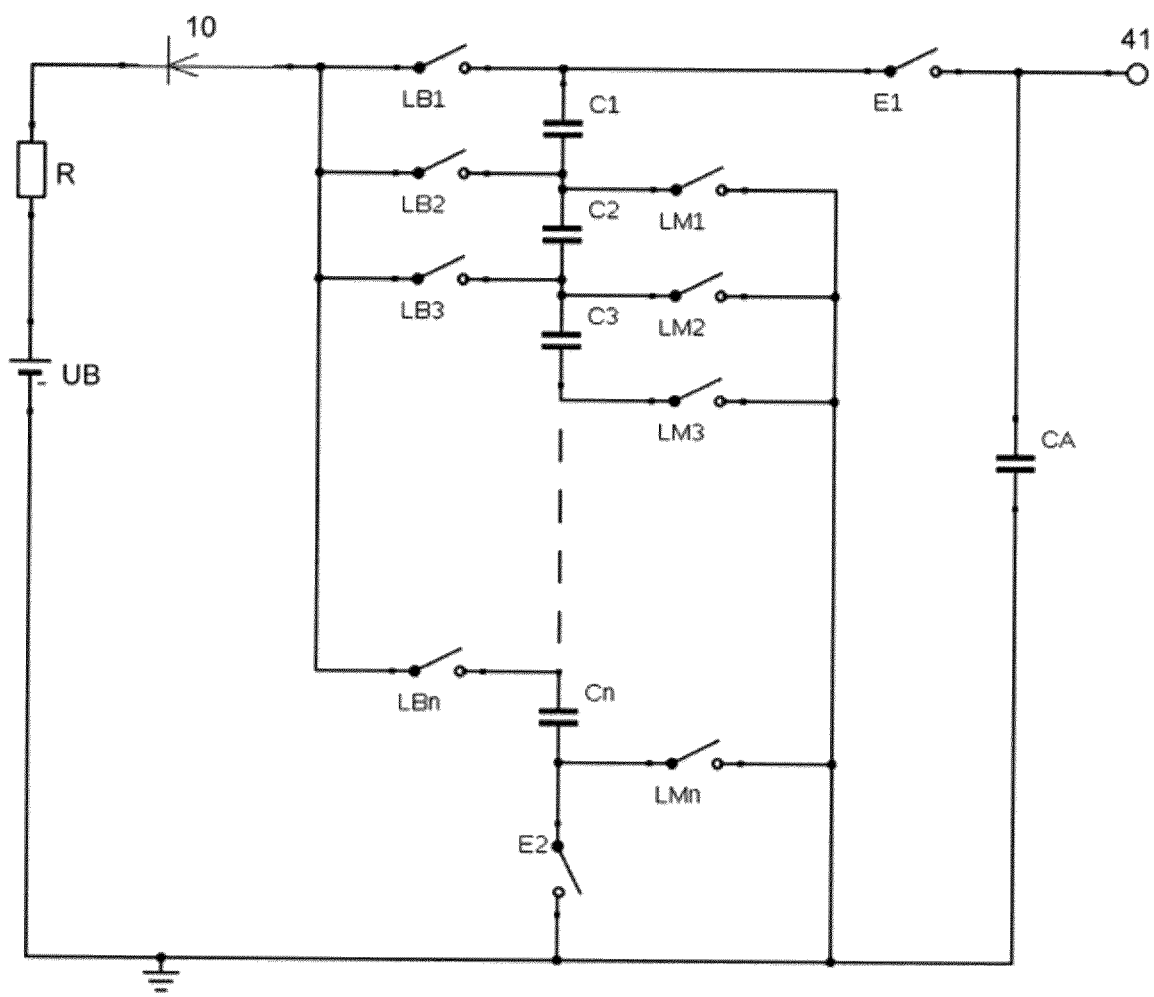
Figure 9:
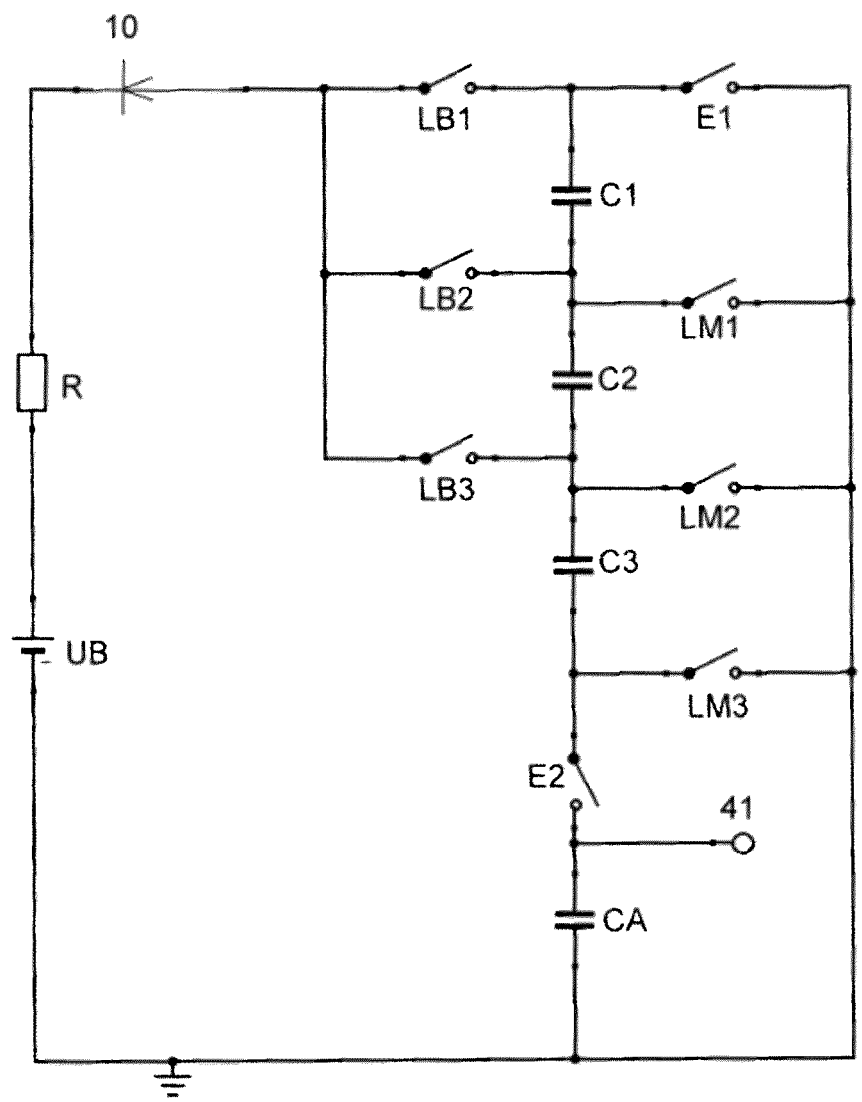
Figure 10:
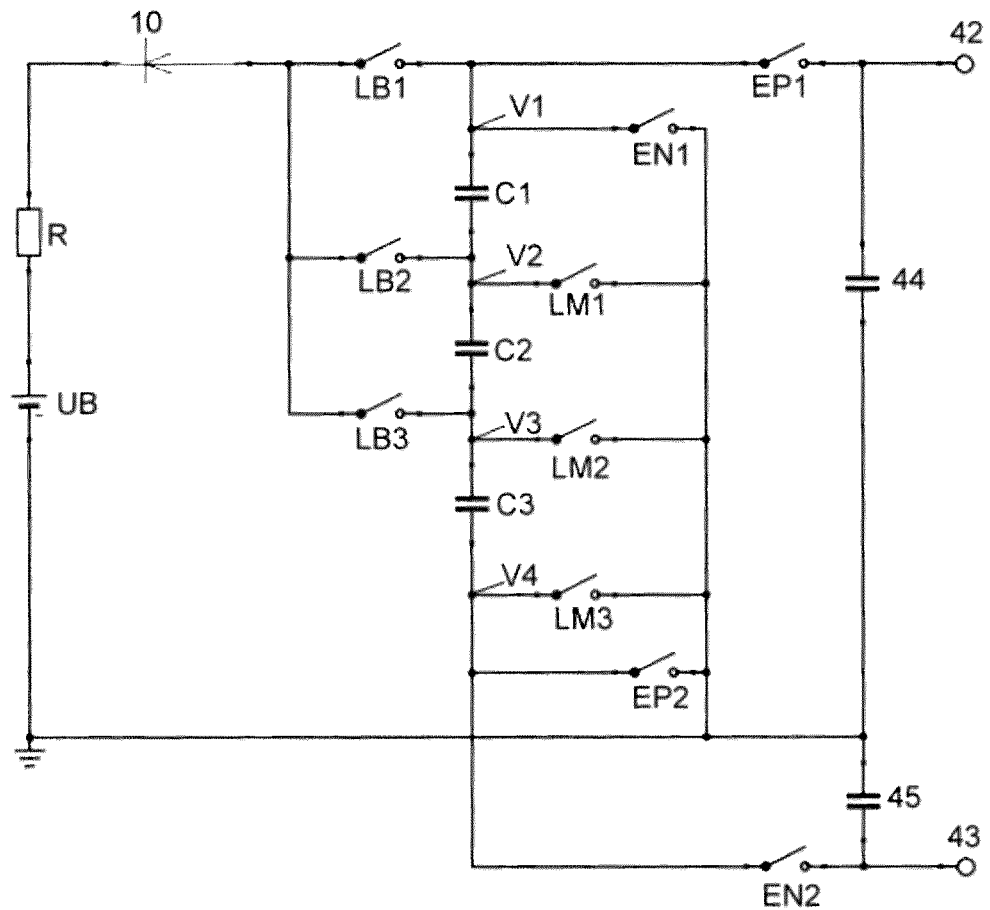
Figure 12A:
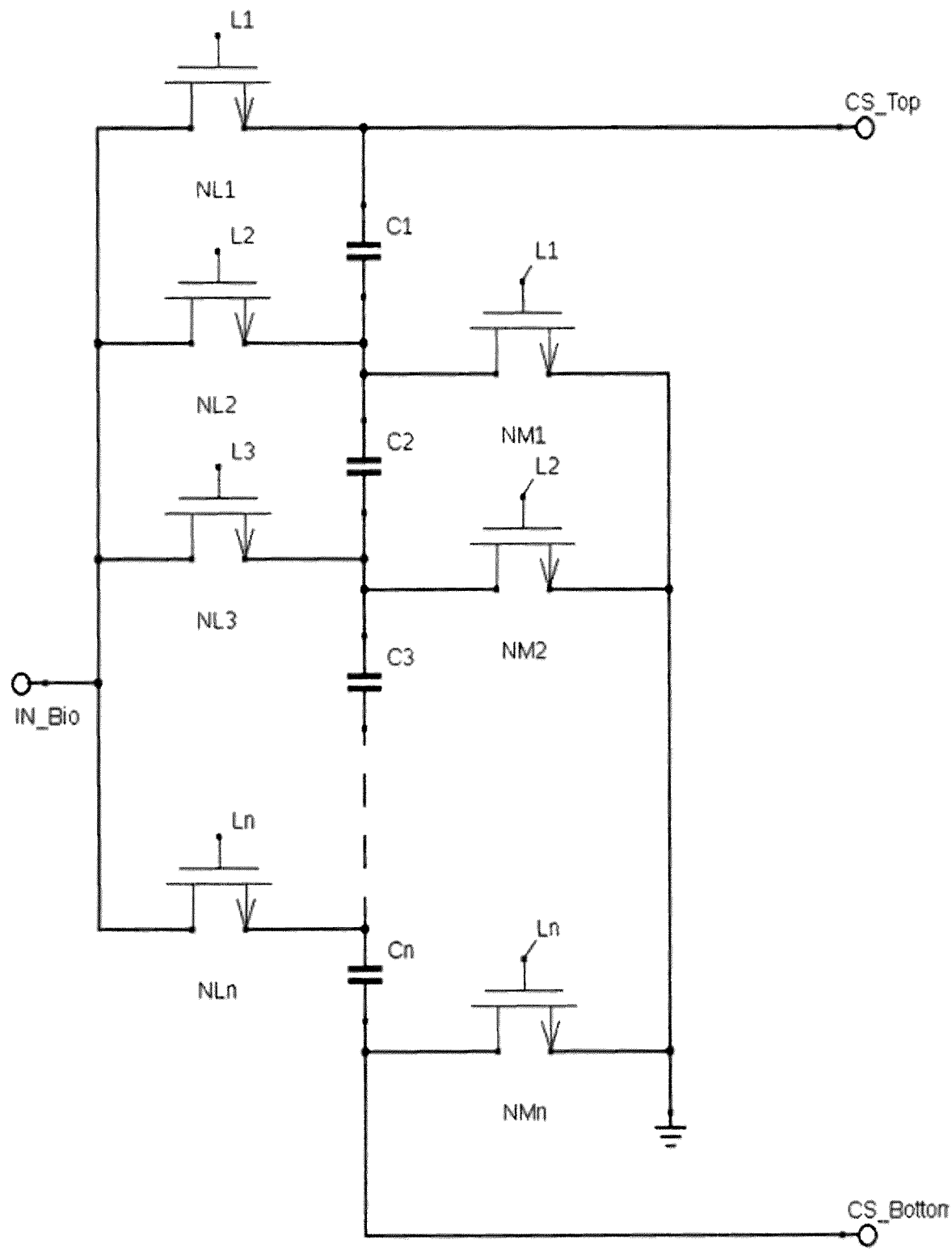
Figure 12B:
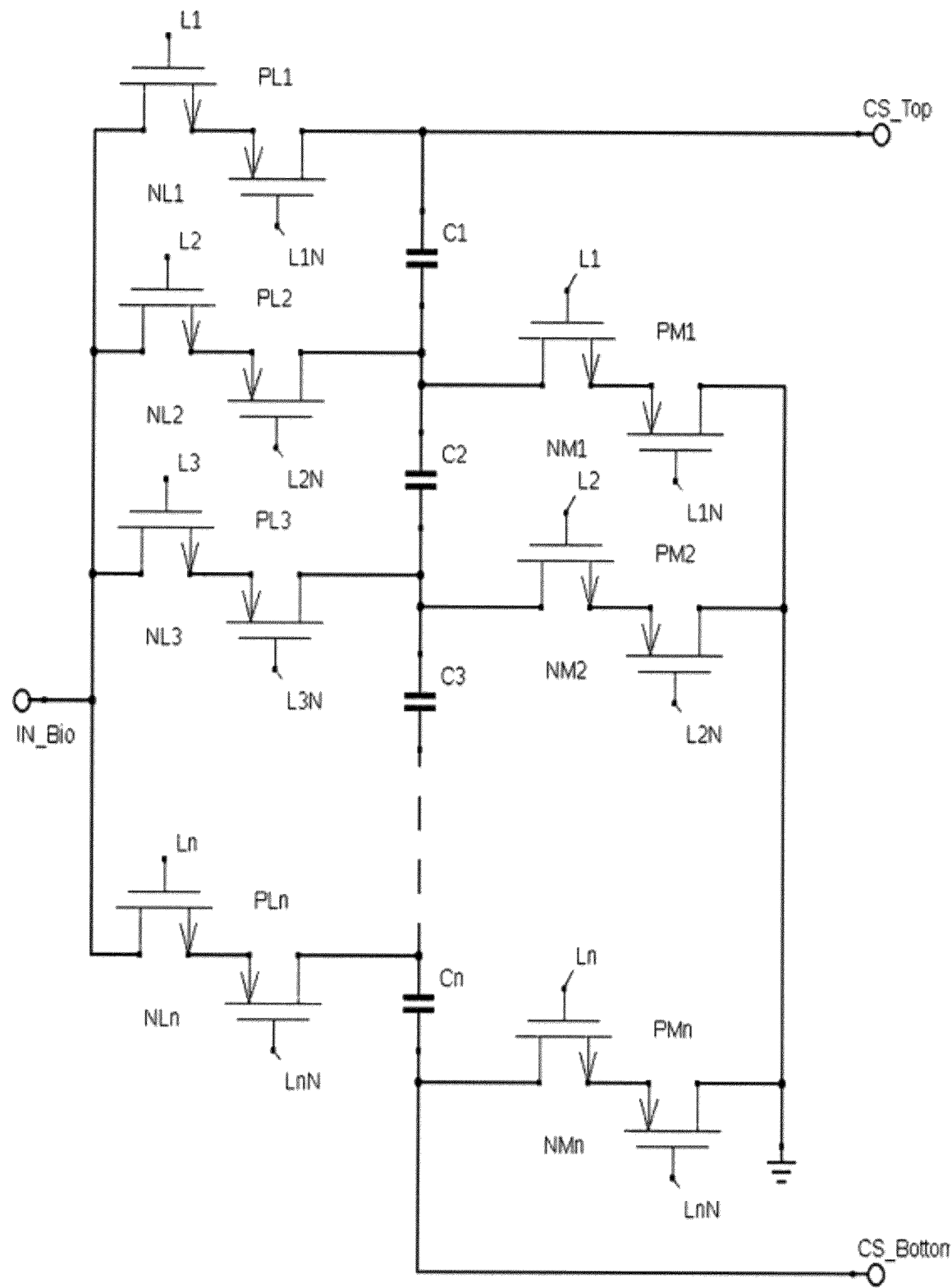
Figure 13:
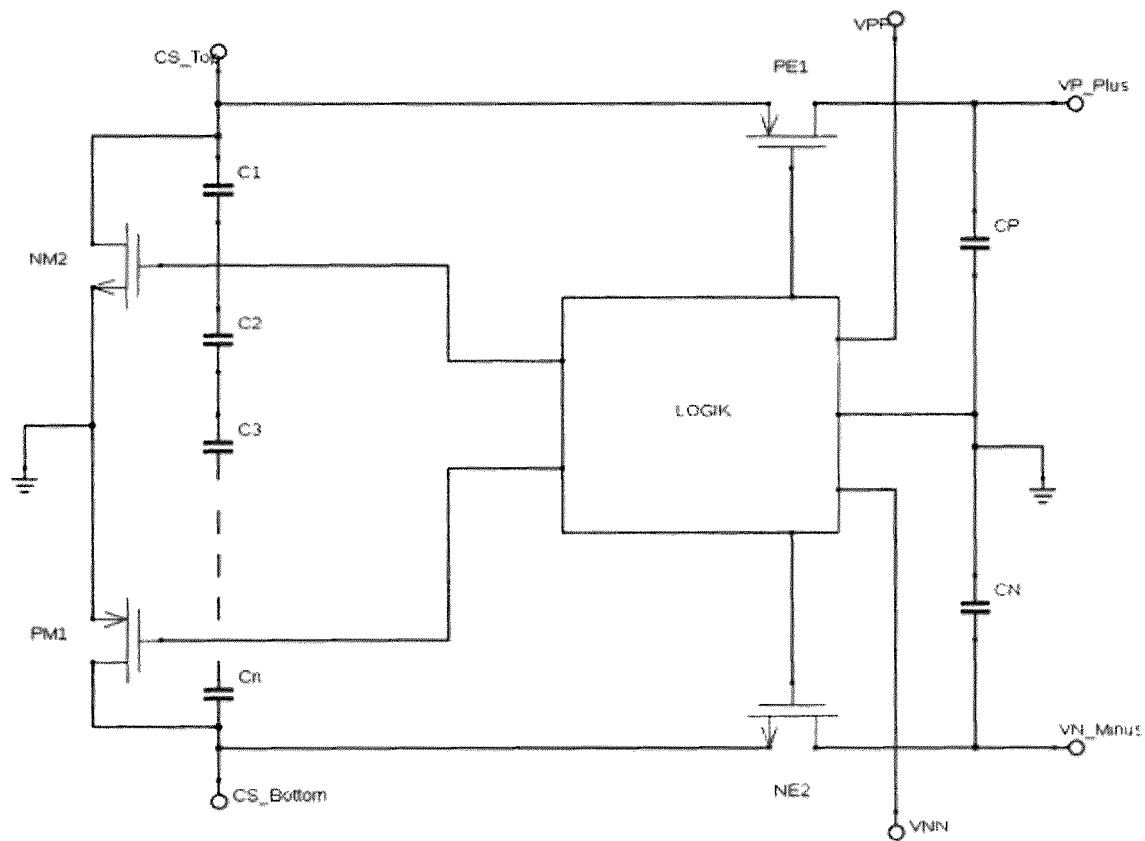

FIGS. 3A and B show a capacitor stack comprising an inductor;

FIG. 4 shows a needle bed as DC input source;

FIG. 5 show the device comprising an additional coil;

FIG. 6 illustrates the device comprising two capacitor stacks;

FIG. 7 shows an electrical circuit for charging and discharging of 3 capacitors of a capacitor stack;

FIG. 8 shows an electrical circuit for charging and discharging of n capacitors of a capacitor stack (A) and the timing of the switches (B);

FIG. 9 shows an electrical circuit for charging 3 capacitors of a capacitor stack with negative voltages and discharging them;

FIG. 10 shows an electrical circuit for charging 3 capacitors of a capacitor stack with negative or positive voltages and discharging them;

FIG. 11 shows the timing of the switches (A) and a simplified timing of the voltage of the capacitances (B) during charging of 3 capacitors of a capacitor stack with negative and positive voltages and discharging them;

FIG. 12 shows an electrical circuit with integrated transistors for charging the capacitors with positive voltage (A) and for charging the capacitors with positive or negative voltages (B);

FIG. 13 shows bipolar discharge of a capacitor stack.

Figure 1:
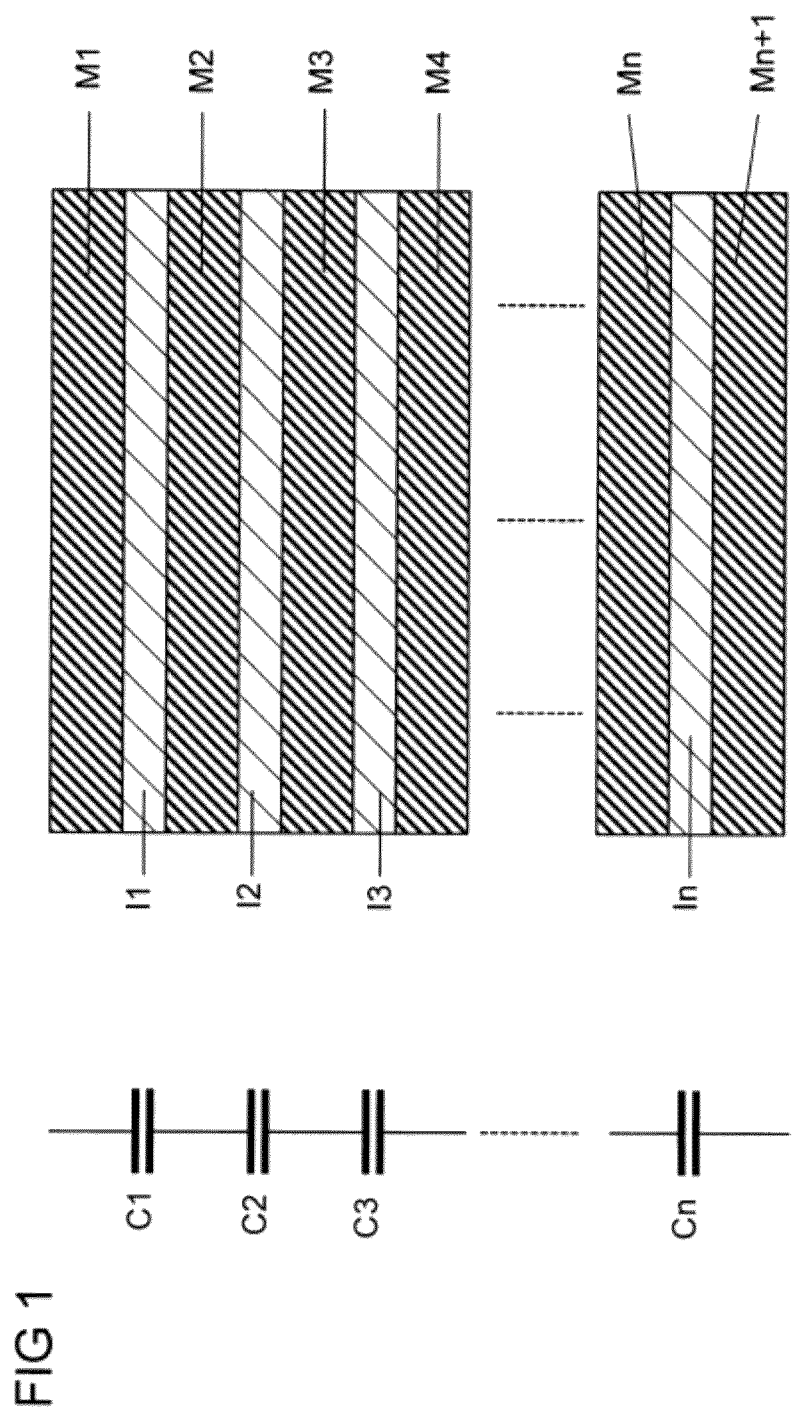
FIG. 1 illustrates the capacitors of a capacitor stack.

FIG. 1 illustrates the structure of a capacitor stack according to the invention. M1 to Mn+1 are conductive plates which are separated by layers of isolating material I1 to In. Thus, a first capacitor C1 is built by the bottom-side of the conductive plate M1, the isolating material layer I1 and the top-side of the conductive plate M2. The neighboring capacitor C2 is built by the bottom-side of the conductive plate M2, the isolating material layer I2 and the top-side of the conductive plate M3. Further capacitors are built in the same way up to the capacitor Cn which is built by the bottom-side of the conductive plate Mn, the isolating layer In and the top-side of the conductive plate Mn+1. Thus by using a capacitor stack according to the invention only the top-side of the conductive plate M1 and the bottom-side of the conductive plate Mn+1 have substantial interfaces to the surrounding, at which parasitic capacitances will arise.

Figure 2:
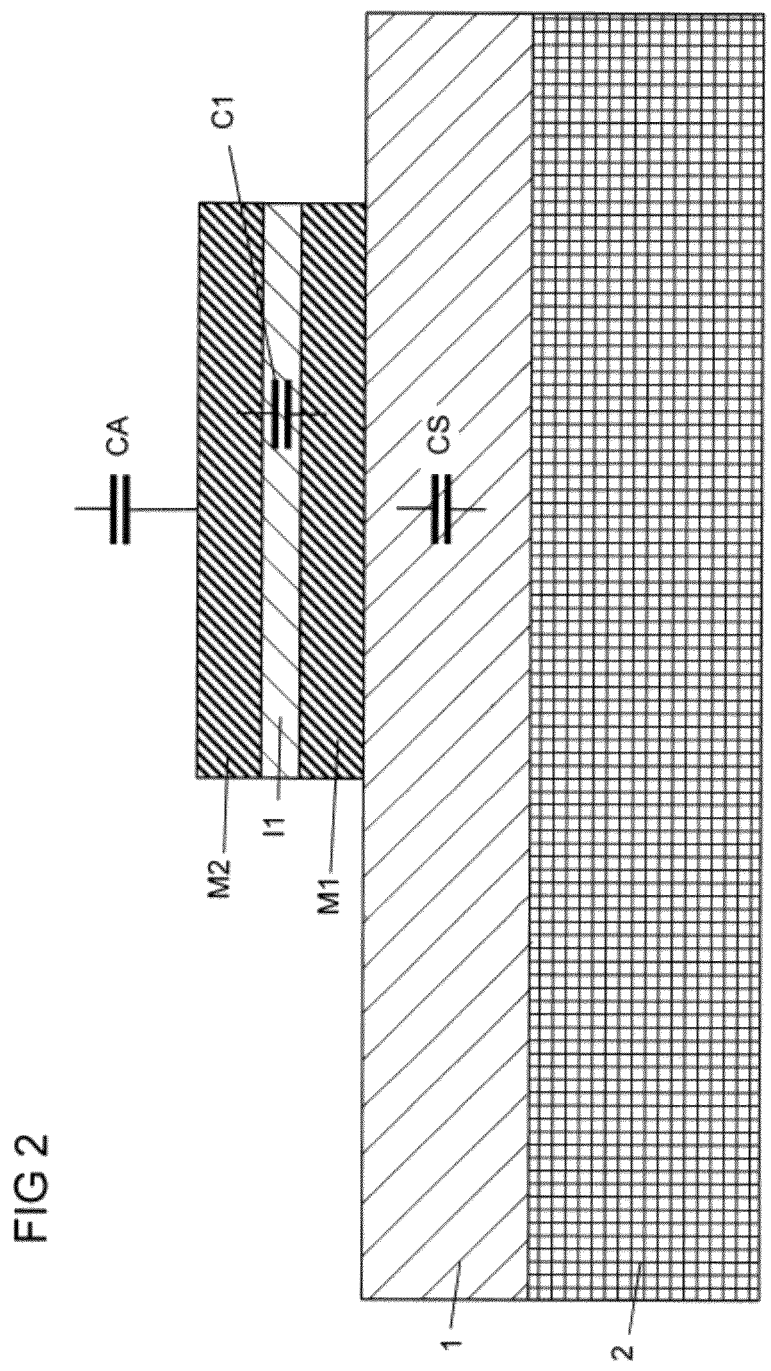
FIG. 2 shows a general MIM-Capacitance with parasitic capacitance to ground.

The structure of a MIM-Capacitor according to the state of the art is illustrated in FIG. 2. The conductive plates M2 and M1 are separated by a layer of isolating material I1, forming the capacitor C1. The top-side of the conductive plate M2 has an interface to the surrounding air, whereby a parasitic capacitance CA is arises. Furthermore, the bottom-side of the conductive plate M1 has an interface to an isolator 1 and a substrate 2. In case of a MIM-Capacitor the isolator 1 is made of $SiO_2$ and the substrate 2 is made of silicon. Also at this interface a parasitic capacitance CS arises. According to the state of the art at every capacitor two parasitic capacitances arise which lowers the charging efficiency of the capacitor.

The charging efficiency is increased by using the design of a capacitor stack according to the invention. The capacitor stack is built by n capacitors, wherein the capacitor stack comprises at least three conductive plates wherein at least one conductive plate is part of a first capacitor and the bottom-side of the conductive plate is part of a neighboring second capacitor. By using this design, no longer two parasitic capacitances arise for every capacitor in the capacitor stack due to interfaces to the surrounding. Instead two substantial parasitic capacitances arise, namely one on the interface of the top conductive plate of the capacitor stack to the surrounding and a second at the interface of the bottom conductive plate of the capacitor stack to the surrounding.

Figure 3B:
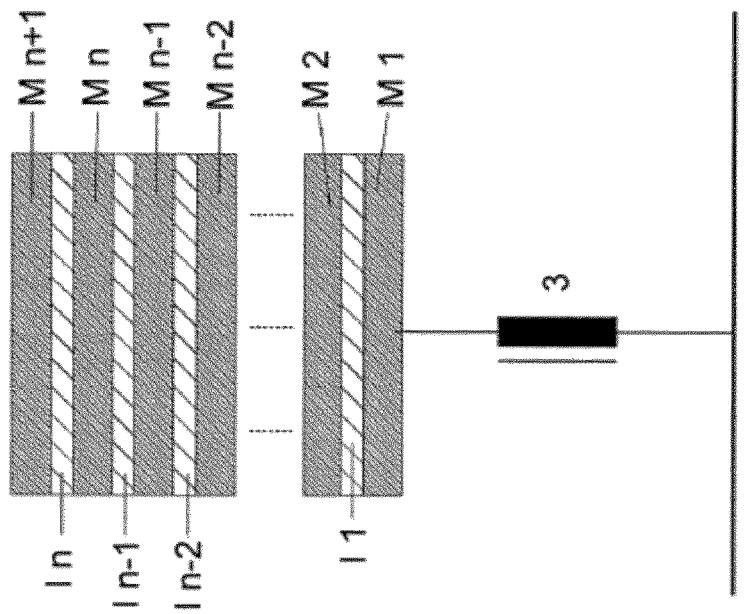

In view not to lose the energy stored in the parasitic capacitors built by the capacitor stack with the surrounding, in one embodiment the invention comprises an inductor as shown in FIGS. 3 (A) and (B). FIG. 3 (A) illustrates the capacitor stack with its typical layered design, wherein M1 to Mn+1 are conductive plates and I1 to In are layers of isolating material. Connected to the capacitor stack is an inductor 3. FIG. 3 (B) illustrates the parasitic capacitance arising from the capacitor stack as a whole as one parasitic capacitor 4 and the inductor 3 as part of an electrical circuit.

In one embodiment of the invention a needle or a needle bed in contact with nerve cells is used as DC input source. FIG. 4 shows a needle bed formed by several needles 10 which are fixed by a needle support 11. Every needle 10 is connected to a capacitor stack by a bump 12. Using an integrated circuit the capacitor stacks are arranged on a microchip 13. The design according to the invention enables to harvest energy from multiple nerve cells.

To make sure the CMOS-logic of the device can work, a startup is required to power the CMOS-logic. Therefore in one embodiment of the invention (shown in FIG. 5) the device additionally comprises a coil 22, which is dedicated to receive a startup energy by magnetic coupling with another external coil 21, whereby the external coil 21 is connected to an AC voltage source 20. The coil 22 is connected to other parts 23 of the device in a way that the CMOS-logic can be powered with energy over the magnetic field, thus providing energy for startup.

FIG. 6 shows an embodiment of the invention, wherein the device comprises two capacitor stacks 31, 32. The electrical circuits of the capacitors stacks are illustrated as grey blocks 30, 33. The first capacitor stack 31 is charged by the small charges collected from the source UB of nerve cells by a needle 10, wherein the nerve tissue has a resistance R. The capacitors of the capacitor stack are charged according to the invention until all capacitors of the capacitor stack 31 are charged. The first capacitor stack 31 is connected to the second capacitor stack 32 and its electrical circuit 33 by switches E1 and E2. If E1 and E2 are closed one capacitor of the capacitor stack 32 is charged by the capacitors of the capacitors stack 31 at once. In the next step the capacitors of the capacitor stack 31 are charged again by the source UB and after all capacitors of capacitor stack 31 are charged they are discharged at once in a further capacitor of capacitor stack 32, by closing switches E1 and E2 in an appropriate manner. This charging scheme is repeated until all capacitors of capacitor stack 32 are charged. Next all capacitors of capacitor stack 32 are discharged at once in a further capacitor 34 outside the capacitor stacks by closing the switches E3 and E4. The output voltage is illustrated as UE. Preferably the capacitors of the capacitor stacks are charged one after the other by charging always neighboring capacitors. Naturally, the charging and discharging scheme of the device according to the invention is used in analogue manner if the device comprises more than two capacitor stacks, e.g. up to 20 capacitor stacks.

The electrical circuit of one embodiment of the device is illustrated in FIG. 7. In this embodiment the device comprises one capacitor stack which is built by three capacitors C1, C2, C3 and switches LB1, LB2, LB3, LM1, LM2 and LM3. Two additional switches E1 and E2 outside the capacitor stack, one further capacitor CA outside the capacitor stack and a DC input source UB. As DC input source UB a needle 10 is used which collects small charges form nerve cells, the resistance of the nerve tissue is illustrated as R. The capacitors are all stacked up according to the invention and are charged sequentially. Capacitor C1 is charged by closing switches LB1 and LM1 simultaneously. Then the switches are opened and C2 is charged by closing switches LB2 and LM2. In a third cycle switches LB3 and LM3 are closed to charge capacitor C3. Discharge of the pumped voltage of the capacitor stack into the one further capacitor CA is achieved by closing E1 and E2. Accordingly, capacitor CA is charged by the capacitors of the capacitors stack (C1, C2, C3) at once and functions as a buffer capacitor. The circuit of FIG. 3 requires one more cycle than capacitors in the capacitor stack, meaning in this particular case 3 cycles are required for the charging of C1, C2 and C3 and one additional cycle to discharge the stack into capacitor CA. The exit is marked with reference sign 41.

The electrical circuit can be used in the same way for any number of capacitors in the capacitor stack. Each additional capacitor in the capacitor stack has to be complemented with two additional loading switches. Also this means that for each additional capacitor in the capacitor stack, an additional loading cycle has to be introduced. The appropriate electrical circuit is shown in FIG. 8 (A) for a capacitor stack with n capacitors illustrated as C1, C2, C3 up to Cn. The timing of the switches is illustrated in FIG. 8 (B). The graph shows the status of the switches depending on the time t. Closed state of the switches is illustrated as a box. One charging cycle of all capacitors in a capacitor stack including discharging all capacitors into a further capacitor outside the capacitor stack is marked with reference sign 50. As can be seen, firstly switches LB1 and LM1 are closed to charge capacitor C1. Next, LB1 and LM1 are opened and LM2 and LB2 are closed to charge C2, and so on until LBn and LMn are closed to charge capacitor Cn. Afterwards switches E1 and E2 are closed to discharge all capacitors of the capacitor stack at once into a further capacitor outside the capacitor stack. The discharging is additionally marked with reference sign 51.

The device according to the invention is also able to generate negative readout voltages. Therefore, an electrical circuit according to FIG. 9 is used. The device shown comprises three capacitors (C1, C2, C3) in the capacitor stack. All reference signs correspond to the reference signs already used in the electrical circuit shown in FIG. 8. To generate negative voltages the charging order of the capacitors of the capacitor stack is reversed. Which means in this case firstly C3 is charged, next C2 and afterwards C1. For this the top plate is connected to ground by closing E1. Capacitances in the capacitor stack are charged sequentially, while one plate is grounded, the other plate is charged to a fraction of the input voltage. This means that capacitances in the capacitor stack above the currently grounded plate are pushed to positive voltages, whereas capacitances below the currently grounded plate are pushed to negative voltages. As already described, preferably the capacitors of the capacitor stack are charged one after the other, wherein always neighboring capacitors are charged.

Parasitic capacitances from the top and from the bottom conductive plates of the capacitor stack (making the largest contribution to the parasitic capacitances of the device) have also to be charged at each charging cycle. For this reason it is most advantageous to always load neighboring capacitors in the capacitor stack. Therefore, it is most favorable to combine the generation of positive and negative voltages. A suitable electrical circuit is illustrated in FIG. 10. After charging the three capacitors C1, C2 and C3 of the capacitor stack sequentially in the this order, switches EP1 and EP2 are closed simultaneously to discharge the capacitors of the capacitor stack to further capacitor 44 outside the capacitor stack. By doing this, capacitor 44 is charged to a positive voltage. Then the sequential charging of the capacitors of the capacitor stack is reversed, meaning firstly C3 is charged, next C2 and afterwards C1. By simultaneously closing switches EN1 and EN2 the capacitors of the capacitor stack are discharged in further capacitor 45 outside the capacitor stack, effectively charging capacitor 45 to a negative voltage. Positive exit is marked with reference sign 42 and negative exit is marked with sign 43.

The timing for the switches in the electrical circuit shown in FIG. 10 is illustrated in FIG. 11 (A) together with the timing of the voltages (FIG. 11 (B)). During the positive charging cycle 60 the capacitances are charged in the order C1-C2-C3 by closing sequentially LB1, LM1-LB2, LM2-LB3, LM3, followed by a discharging cycle, wherein switches EP1 and EP2 are simultaneously closed. After this, the negative charging cycle is executed in reverse order: C3-C2-C1 by closing sequentially LB3, LM3-LB2, LM2-LB1, LM1 followed by discharging the capacitors of the capacitor stack in capacitor 45 by simultaneously closing switches EN1 and EN2.

FIG. 11 (B) illustrates the timing of the voltage. It should be noted that this is a largely simplified sketch in view to elaborate the principle. The voltage potentials V1 through V4 from FIG. 10 are depicted and correspond to the conductive plates in the capacitor stack. The representation assumes that the circuit charging is settled after many iterations, so that all the capacitors are charged to the full amount and that no output current is unloading the output capacitor 44 or 45, respectively. It can be seen that the entire capacitor stack oscillates and multiplies the voltage from the charging source 64 by the number of capacitors in the capacitor stack. Mass potential is illustrated by line 65, the amount of voltage discharged in capacitor 44 is marked with reference sign 62 while the amount of voltage discharged in capacitor 45 is marked with reference sign 63.

FIG. 7 shows how a metal-isolator stack can be used to construct a compact capacitor stack. The implementation of the switching elements with integrated transistors need to consider the diffusions in the semiconductor material in view to consider the diode effects of the MOS-Transistors. FIGS. 12 (A) and (B) show the partial circuit for charging of the capacitor stack from FIG. 7 when it is realized with integrated transistors. The regularity is visible and also the capability to extend the capacitor stack to n capacitors. The capacitor stack generates positive as well as negative voltage, depending whether the top plate or the bottom plate is grounded. There are two mechanisms to make sure that the non-selected transistors do not open.

FIG. 12 (A) employs gate voltages between the most positive and the most negative potential in the stack. Also, when using bulk-technology, all p-substrates (of the NMOS-transistors) have to be tied to the most negative voltage in the circuits as otherwise Source/Bulk or Drain/Bulk diode action may disturb the functionality. For SOI- and FDSOI-Technologies this constraints does not exist due to the absence of the bulk-diode.

In FIG. 12 (B) both positive and negative voltages are being used. Here the gates of the NMOS-transistors are switched with voltages between 0 and positive supply and the PMOS-transistors are switched between 0 and the negative supply. With this, the non-selected path to the capacitor stack is always open in the sense of not connected. The selected path puts positive supply to NLn and NMn, while PLn and PMn receive the negative supply voltage.

Discharge occurs from the top- and bottom-plates of the capacitor stack where the sum of the individual capacitor-voltages can be found. Discharging of a positive or a negative voltage depends on whether the top-conductive plate or the bottom-conductive plate is grounded. A suitable discharge circuit is depicted in FIG. 13.

While the bottom-conductive plate is grounded through PM1, the top-conductive plate of the capacitor stack is connected through PE1 to the buffer-capacitor CP outside the capacitor stack. PM1 and PE1 are both activated when their gates are connected to the negative supply (VNN). To block the paths through those transistors, the gates are both being pulled to the positive supply (VPP).

To read out negative voltage, the top-conductive plate is grounded through NM2 and the bottom-conductive plate is connected through NE2 to the buffer-capacitor CN outside the capacitor stack. Both NMOS-transistors are activated when their gate-voltage is pulled to the positive supply VPP. For blocking, both gate potential are pulled to negative supply (VNN).

Example 1

A device according to the invention with one capacitor stack comprising 9 capacitors is connected to an input voltage source of 10 mV. The inner resistance of the voltage source is 100 kOhm. Every capacitor of the capacitor stack has a capacitance of 100 pF and is charged to 90%. The cycle time for charging one capacitor is 25 µs. The stack of 9 capacitors requires in general a cycle time of 250 µs (9 charging cycles+1 discharge cycle of 25 µs). The input of 10 mV generates an output of 81 mV. This is one setting applied for harvesting of bioelectric energy.

Example 2

A device according to the invention comprising two capacitor stacks is connected to an input voltage source of 10 mV. Each capacitor stack comprises 10 capacitors with a capacitance of 100 pF. According to the invention the capacitors of the capacitor stacks are charged one after the other to 100%, which is maximum efficiency. Therefore every capacitor of the first stack is charged to 10 mV. After all capacitors of the first capacitor stack are charged, all capacitors of the first capacitor stack are discharged into the top capacitor of the second capacitor stack. Accordingly, the top capacitor of the second capacitor stack is charged to 100 mV. Next, the capacitors of the first capacitor stack are charged again one after the other each to 10 mV. Subsequently, all capacitors of the first capacitor stack are discharged into a further capacitor of the second capacitor stack, whereby the further capacitor of the second capacitor stack is a neighboring capacitor of the capacitor of the second capacitor stack which was charged before. This scheme is repeated until all capacitors of the second capacitor stack are charged. Afterwards, all capacitors of the second capacitor stack are discharged into a buffer capacitor outside the capacitor stack. By this method a maximum output of 1V is realized. This example shows an embodiment, where cascading of the charge collection generates significant higher voltages than the initial input source provides as voltage.

Example 3

The same device as described in example 2 is used with a charging efficiency of 50% of each capacitor in the first and second capacitor stack. With an input voltage source of 10 mV, an output voltage of 250 mV is realized. This embodiments is provided when charging times are shortened so that the capacitors are charged incompletely.

REFERENCE LIST

C1, C2, C3, . . . , Cn capacitors
I1, I2, I3, . . . In isolating material
M1, M2, M3, . . . , Mn, Mn+1 conductive plates
CA, CS capacitance
1 isolator
2 substrate
3 inductor
4 capacitor
10 needle
11 needle support
12 bump
13 microchip
20 AC voltage source
21 external coil
22 coil
23 parts of the device
UB voltage source
R resistance
30, 32 electrical circuits of capacitor stacks
31, 32 capacitor stack
UE output voltage
LB1, LB2, LB3, . . . , LBn switches
LM1, LM2, LM3, . . . , LMn switches
E1, E2 switches
41 exit
50 charging cycle
51 discharging into a further capacitor
EN1, EN2, EP1, EP2 switches
42 positive exit
43 negative exit
44, 45 capacitors
60 positive charging cycle
61 negative charging cycle
62, 63 voltage discharged
64 voltage of charging source
65 mass potential
L1, L2, L3, . . . , Ln transistors
NL1, NL2, NL3, . . . , NLn transistors
NM1, NM2, NM3, . . . , NMn transistors
PL1, PL2, PL3, . . . , PLn transistors
L1N, L2N, L3N, . . . , LnN transistors
PM1, PM2, PM3, . . . , PMn transistors
PE1, NE1 transistors
IN_Bio voltage source
CS_Top top plate potential
CS_Bottom bottom plate potential
VPP positive supply
VNN negative supply
VP_Plus positive output voltage
VN_Minus negative output voltage

The invention claimed is:

1. Device for charge collection comprising
at least one capacitor stack built by n capacitors and 2n switches;
at least one further capacitor outside the at least one capacitor stack as buffer capacitor;
at least two additional switches outside the at least one capacitor stack;
a DC input source;
a CMOS-Logic;
wherein the 2n switches of the at least one capacitor stack couple the n capacitors selectively to the DC input source;
wherein the n capacitors of the at least one capacitors stack are dedicated to be sequentially charged by the DC input source one after the other;
wherein the at least one further capacitor outside the at least one capacitors stack is dedicated to be charged from the n capacitors of the capacitor stack at once; and
wherein n∈N.

2. Device according to claim 1, characterized in that the capacitor stack comprises at least three conductive plates, wherein the conductive plates have a top-side and a bottom-side; and wherein the top-side of at least one conductive plate is part of a capacitor and the bottom-side of the at least one conductive plate is part of a neighboring capacitor.

3. The device according to claim 1, characterized in that the device is an integrated circuit wherein switches are realized as transistors and capacitors are realized by conductive plates from integrated circuit technology.

4. The device according to claim 1, characterized in that the device comprises two further capacitors outside the capacitor stack as buffer capacitors outside the at least one capacitors stack and four additional switches outside the at least one capacitor stack.

5. The device according to claim 1, characterized in that the device comprises additionally an inductor.

6. The device according to claim 1, characterized in that the device comprises several capacitor stacks wherein each said capacitor stack is dedicated to charge another capacitor stack and one capacitor stack is dedicated to charge at least one further capacitor outside the capacitor stacks.

7. The device according to claim 1, characterized in that the DC input source is a needle bed in contact with nerve cells, wherein needles of the needle bed are isolated against each other and connected through to the back-side by a soldering bump.

8. The device according to claim 7, characterized in that the DC input source is a needle bed in contact with nerve cells, wherein every needle of the needle bed is connected to a capacitor stack by a soldering bump.

9. The device according to claim 1, characterized in that the device additional comprises a coil, which is dedicated to receive a startup energy by magnetic coupling with another coil.

10. The device according to claim 1 wherein the DC input source is bioelectric signals from nerve potential.

11. Method for charge collection, comprising at least one capacitor stack build by n capacitors and 2n switches, at least one further capacitor outside the capacitor stack as buffer capacitor, at least two additional switches and a DC input source, comprising the steps the n capacitors of the capacitor stack are sequentially charged by coupling one capacitor after the other to the DC input source by selectively closing the switches;

discharging the n capacitors of the capacitor stack into the at least one further capacitor outside the capacitor stack;

wherein $n \in N$.

12. The method according to claim 11, characterized in that the n capacitors of the capacitor stack are sequentially charged one after the other in n charging cycles and that the n capacitors of the capacitor stack are discharged in an $n+1^{st}$ cycle into the at least one further capacitor outside the capacitor stack at once.

13. The method according to claim 11, characterized in that the n capacitors of the capacitor stack are sequentially charged one after the other in n charging cycles, wherein the first capacitor is charged, afterwards the capacitor which is next to the first one is charged, afterwards the capacitor which is next to the one charged before is charged until all n capacitors are charged.

14. The method according to claim 13, characterized in that after the n capacitors of the capacitor stack are sequentially charged the n capacitors are discharged into a first further capacitor outside the capacitor stack; afterwards the n capacitors of the capacitor stack are sequentially charged in a reversed order and after the n capacitors are charged the n capacitors are discharged into a second further capacitor outside the capacitor stack.

15. The method according to claim 11, characterized in that the n capacitors of a capacitor stack are discharged at once into one capacitor of a further capacitor stack.

16. The method according to claim 11, characterized in that bioelectric signals from nerve potential are used as DC input.

* * * * *